(12) United States Patent
Tsuchiya (10) Patent No.: US 10,190,975 B2
(45) Date of Patent: Jan. 29, 2019

(54) LEAKED GAS DETECTION DEVICE AND LEAKED GAS DETECTION METHOD

(71) Applicant: KONICA MINOLTA, INC., Chiyoda-ku (JP)

(72) Inventor: Shinsuke Tsuchiya, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/771,861

(22) PCT Filed: Oct. 19, 2016

(86) PCT No.: PCT/JP2016/080956
§ 371 (c)(1),
(2) Date: Apr. 27, 2018

(87) PCT Pub. No.: WO2017/073427
PCT Pub. Date: May 4, 2017

(65) Prior Publication Data
US 2018/0321141 A1 Nov. 8, 2018

(30) Foreign Application Priority Data
Oct. 29, 2015 (JP) ................................ 2015-212507

(51) Int. Cl.
G01N 21/35 (2014.01)
G01N 21/3504 (2014.01)
G01N 33/00 (2006.01)
G01N 21/85 (2006.01)

(52) U.S. Cl.
CPC ......... *G01N 21/3504* (2013.01); *G01N 21/85* (2013.01); *G01N 33/0059* (2013.01); *G01N 2021/3545* (2013.01)

(58) Field of Classification Search
None
See application file for complete search history.

(56) References Cited

U.S. PATENT DOCUMENTS 5,306,913 A 4/1994 Noack et al.
2010/0231722 A1 9/2010 Hill, Jr. et al.
2016/0320296 A1* 11/2016 Asano ................. G01J 5/0014

FOREIGN PATENT DOCUMENTS

JP 4-93745 3/1992
JP 2015-99168 5/2015
WO WO 03/044499 5/2003

* cited by examiner

*Primary Examiner* — Edwin Gunberg
(74) *Attorney, Agent, or Firm* — Cozen O'Connor (57) ABSTRACT

In a leaked gas detection device and a leaked gas detection method according to the present invention, a gas cloud image area of a gas cloud formed with a leaked gas is extracted on the basis of an infrared image of a target area, a gas temperature of the gas cloud is acquired, a concentration-thickness product of the gas cloud is obtained, and a reliability degree that is an index representing the degree of reliability with respect to the obtained concentration-thickness product of the gas cloud is obtained on the basis of a background temperature in the gas cloud image area and the gas temperature of the gas cloud.

14 Claims, 6 Drawing Sheets

LEAKED GAS DETECTION DEVICE AND LEAKED GAS DETECTION METHOD

RELATED APPLICATIONS

This is a U.S. National Phase Application under 35 USC 371 of International Application PCT/JP2016/080956 filed on Oct. 19, 2016.

This application claims the priority of Japanese application no. 2015-212507 filed Oct. 29, 2015, the entire content of which is hereby incorporated by reference.

TECHNICAL FIELD

The present invention relates to a leaked gas detection device and a leaked gas detection method for detecting a predetermined gas leaked into a space, and more particularly to a leaked gas detection device and a leaked gas detection method for enabling a user to determine the degree of reliability with respect to an obtained concentration-thickness product of a leaked gas.

BACKGROUND ART

For example, when gases such as a flammable gas, a toxic gas, and vapor of an organic solvent are leaked from piping, tank, and the like, the leakage needs to be dealt with early. In addition, to determine the danger, the concentration-thickness product, preferably, the concentration of the leaked gas leaked into a space needs to know. Therefore, devices for measuring a gas such as the leaked gas are demanded. As such devices, for example, Patent Literature 1 discloses a technique for obtaining a concentration-thickness product, and Patent Literature 2 discloses a technique for correcting a concentration-thickness product on the basis of a difference between a predetermined average temperature and a background temperature.

Here, in the technique disclosed in Patent Literature 1 described above, an amount of infrared rays is obtained at two points A and B where background temperatures through the leaked gas are different, by an infrared camera, a value of the concentration-thickness product ct is assigned in the following equation 1, and the concentration-thickness product ct by which both the sides of the following equation 1 become equal is obtained as the concentration-thickness product ct of the leaked gas (second sight method).

$$P_B - P_A = \varepsilon \int \exp(\alpha(\lambda)ct) S(\lambda) [B(T_{back\_B}, \lambda) - B(T_{back\_A}, \lambda)] \, d\lambda \quad (1)$$

Here, $P_A$ is the amount of infrared rays observed by the infrared camera at the point A, $B(T_{back\_A}, \lambda)$ is the amount of background radiation infrared rays at the point A ($T_{back\_A}$ is the background temperature at the point A and $\lambda$ is the wavelength), $P_B$ is the amount of infrared rays observed by the infrared camera at the point B, $(T_{back\_B}, \lambda)$ is the amount of background radiation infrared rays at the point B ($T_{back\_B}$ is the background temperature at the point B), $S(\lambda)$ is the transmittance of an optical system, ct is the concentration-thickness product of the gas (c is the concentration and t is the thickness), $\varepsilon$ is the background emissivity, and $\alpha(\lambda)$ is the gas absorption rate. The integral $\int$ is executed over the wavelength range of observed infrared rays.

By the way, in the technique disclosed in Patent Literature 1 described above, if the difference between the background temperature (the amount of background radiation infrared rays) and the leaked gas temperature is small, a signal regarding the background temperature (the amount of background radiation infrared rays), which is obtained by the infrared camera, becomes small and the signal-to-noise ratio (SN ratio) is decreased. As a result, a large error is included in the concentration-thickness product. For this reason, although the concentration-thickness product may be corrected by the technique disclosed in Patent Literature 2, complicated correction calculation is executed in Patent Literature 2, and therefore information processing of the correction calculation takes time, and a large difference is caused between observation timing by the infrared camera and calculation output timing of the concentration-thickness product, resulting in losing real-time properties. Particularly, the leaked gas needs to be dealt with as soon as possible, the real-time properties are important for calculation of the concentration-thickness product, which serves as an index for determining if it is necessary to deal with the leaked gas as soon as possible.

CITATION LIST

Patent Literature

Patent Literature 1: U.S. Pat. No. 5,306,913
Patent Literature 2: WO 2003/044499

SUMMARY OF INVENTION

The present invention has been made in view of the foregoing, and an objective is to provide a leaked gas detection device and a leaked gas detection method for enabling a user to determine the degree of reliability of a concentration-thickness product while prioritizing real-time properties.

In a leaked gas detection device and a leaked gas detection method according to the present invention, a gas cloud image area of a gas cloud formed with a leaked gas is extracted on the basis of an infrared image of a target area, a gas temperature of the gas cloud is acquired, a concentration-thickness product of the gas cloud is obtained, and a reliability degree that is an index representing the degree of reliability with respect to the obtained concentration-thickness product of the gas cloud is obtained on the basis of a background temperature in the gas cloud image area and the gas temperature of the gas cloud. Therefore, the leaked gas detection device and the leaked gas detection method according to the present invention enable a user to determine the degree of reliability of the concentration-thickness product while prioritizing the real-time properties.

These and other objectives, features, and advantages of the present invention will become clear from the following detailed description and accompanying drawings.

DESCRIPTION OF EMBODIMENTS

Hereinafter, an embodiment of the present invention will be described with reference to the drawings. Note that configurations denoted by the same reference numeral in the drawings indicate the same configuration, and description thereof is omitted as appropriate. In the present specification, in the case of collectively referring to a configuration, a reference numeral without a suffix is denoted, and in the case of individually referring to a configuration, a reference numeral with a suffix is denoted.

Figure 1:
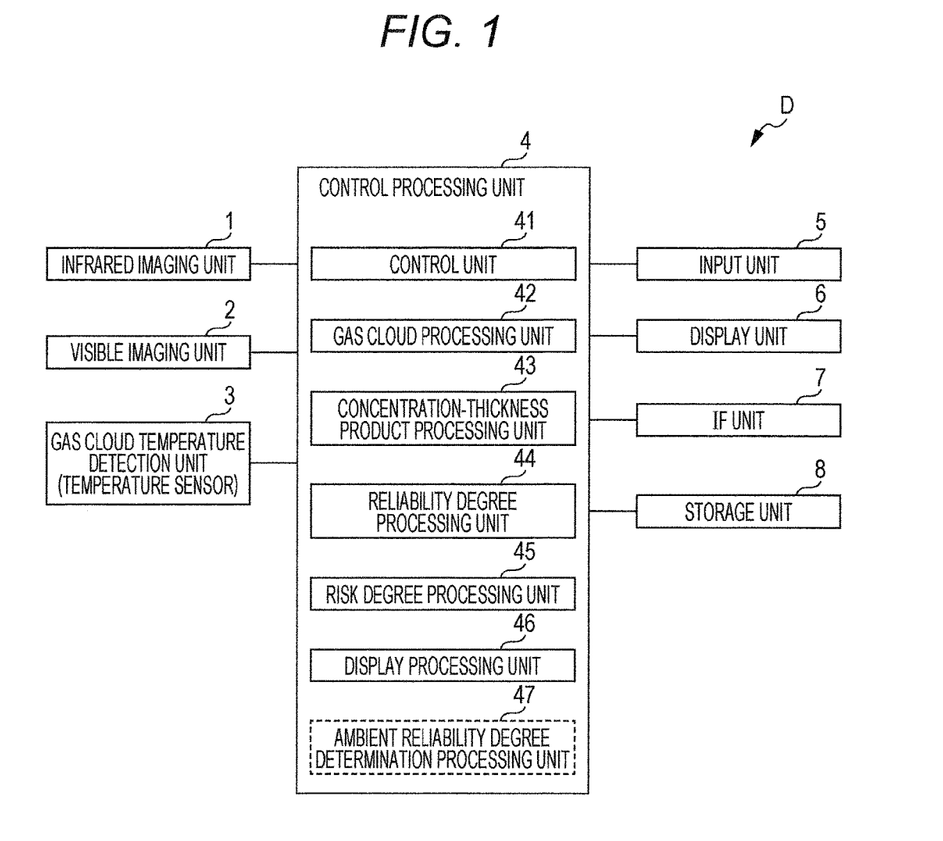
FIG. 1 is a block diagram illustrating a configuration of a leaked gas detection device in an embodiment.
Figure 2:
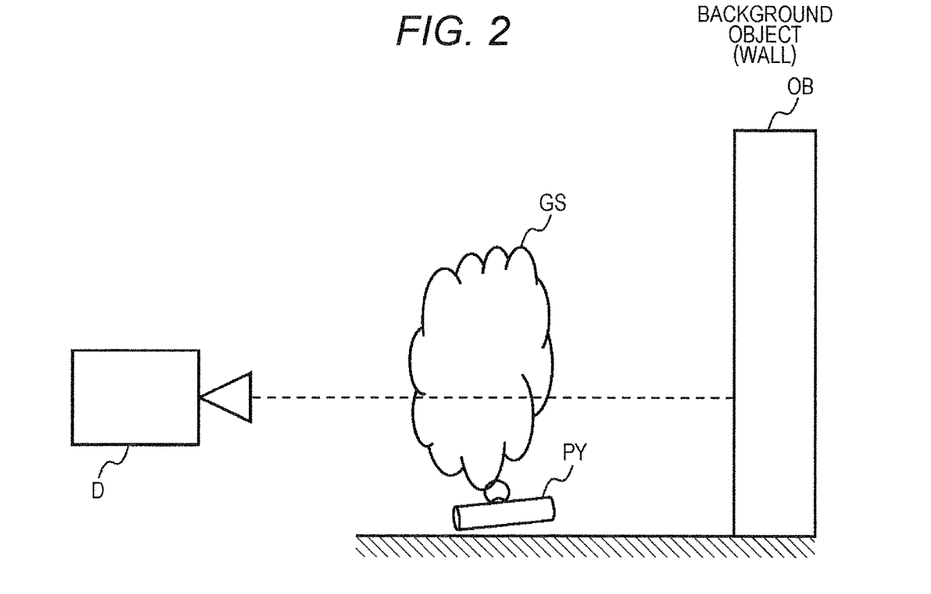
FIG. 2 is a schematic diagram for describing a use state of the leaked gas detection device.
Figure 3:
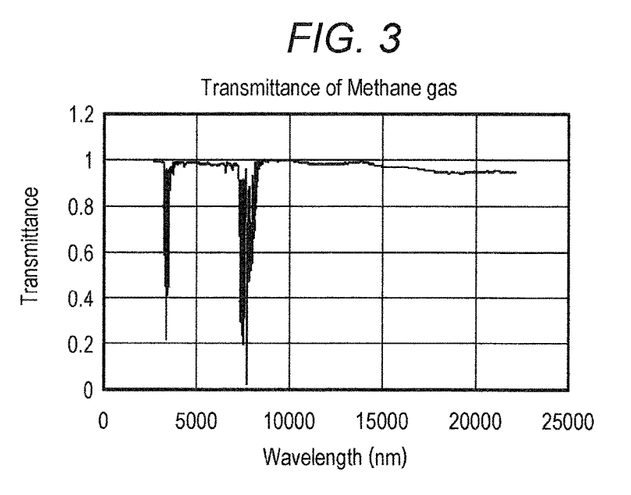
FIG. 3 is a diagram illustrating a characteristic curve of transmittance with respect to a wavelength in methane gas as an example.
Figure 4:
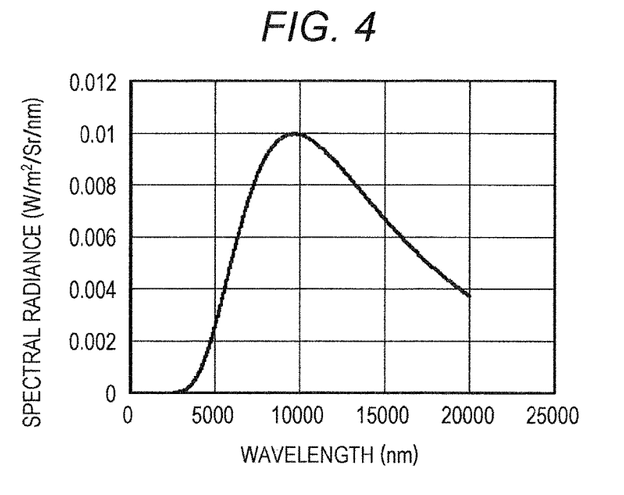
FIG. 4 is a diagram illustrating a characteristic curve of spectral radiance with respect to a wavelength in methane gas as an example.
Figure 5:
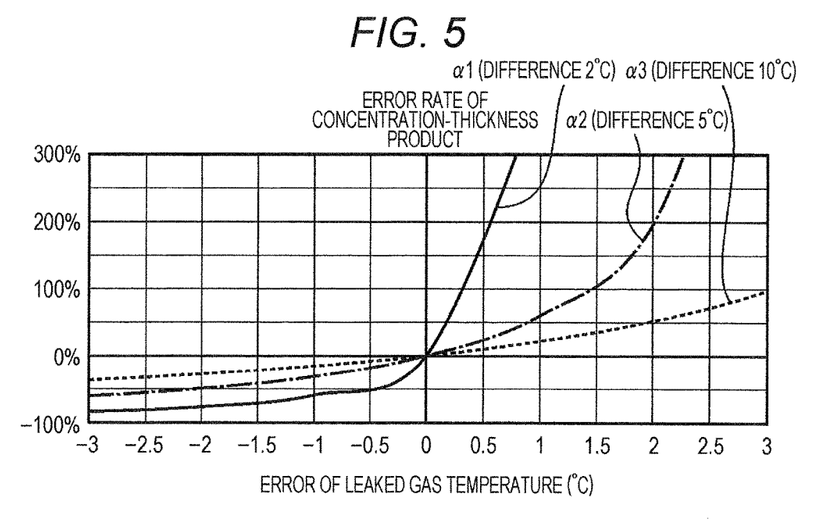
FIG. 5 is a diagram for describing an error included in an obtained concentration-thickness product.

FIG. 1 is a block diagram illustrating a configuration of a leaked gas detection device in an embodiment. FIG. 2 is a schematic diagram for describing a use state of the leaked gas detection device in the embodiment. FIG. 3 is a diagram illustrating a characteristic curve of transmittance with respect to a wavelength in methane gas as an example. In FIG. 3, the horizontal axis represents the wavelength λ expressed in nm, and the vertical axis represents the transmittance τ. FIG. 4 is a diagram illustrating a characteristic curve of spectral radiance with respect to a wavelength in methane gas as an example. In FIG. 4, the horizontal axis represents the wavelength λ expressed in nm, and the vertical axis represents the spectral radiance expressed in $W/m^2/Sr/nm$. FIG. 5 is a diagram for describing an error included in the obtained concentration-thickness product.

The leaked gas detection device according to the embodiment is a device that extracts, from an infrared image of a predetermined target area including a gas pipe (piping) and a gas storage that stores a gas such as a gas tank, a gas cloud image area of a gas cloud formed with a leaked gas of the gas leaked from the gas storage, and obtains a concentration-thickness product in the gas cloud of the extracted gas cloud image area. Then, the leaked gas detection device in the present embodiment is a device that obtains a reliability degree that is an index representing the degree of reliability with respect to the obtained concentration-thickness product. More specifically, the leaked gas detection device in the embodiment includes an infrared image acquisition unit that acquires an infrared image of a target area, a gas cloud processing unit that extracts a gas cloud image area of a gas cloud formed with a leaked gas on the basis of the infrared image of the target area acquired in the infrared image acquisition unit, a gas cloud temperature acquisition unit that acquires a gas temperature of the gas cloud, a concentration-thickness product processing unit that obtains a concentration-thickness product of the gas cloud, and a reliability degree processing unit that obtains a reliability degree that is an index representing the degree of reliability with respect to the concentration-thickness product of the gas cloud obtained in the concentration-thickness product processing unit on the basis of a background temperature in the gas cloud image area extracted in the gas cloud processing unit and the gas temperature acquired in the gas cloud temperature acquisition unit. As illustrated in FIG. 1, a leaked gas detection device D in the present embodiment includes, for example, a control processing unit 4, an interface unit (IF unit) 7, and a storage unit 8, and further includes an infrared imaging unit 1, a visible imaging unit 2, a gas cloud temperature detection unit 3, an input unit 5, and a display unit 6, in the example illustrated in FIG. 1.

The infrared imaging unit 1 is a device connected to the control processing unit 4 and which images a target area in an infrared manner and generates an infrared image of the target area according to control of the control processing unit 4. The infrared imaging unit 1 is, for example, an infrared camera or the like including an imaging optical system that forms an infrared ray optical image (infrared optical image) of the target area on a predetermined image plane, an infrared image sensor disposed with a light receiving surface coincident with the image plane and which converts the infrared ray optical image of the target area into an electrical signal, an infrared image processing unit that generates data of the infrared image by image-processing an output of the infrared image sensor, and the like. The infrared imaging unit 1 outputs the infrared image (data of the infrared image) of the target area to the control processing unit 4.

The visible imaging unit 2 is a device connected to the control processing unit 4 and which images the target area in a visible manner and generates a visible image of the target area according to the control of the control processing unit 4. The visible imaging unit 2 is, for example, a visible camera or the like including an imaging optical system that forms an optical image (an optical image of visible light) of the target area on a predetermined image plane, an image sensor disposed with a light receiving surface coincident with the image plane and which converts the optical image of the target area into an electrical signal, a visible image processing unit that generates data of the visible image by image-processing an output of the image sensor, and the like. The visible imaging unit 2 outputs the visible image (data of the visible image) of the target area to the control processing unit 4.

The gas cloud temperature detection unit 3 is a device connected to the control processing unit 4 and which detects a gas temperature of a gas cloud formed with a leaked gas according to the control of the control processing unit 4. In the present embodiment, to relatively easily detect the gas temperature, the gas cloud temperature detection unit 3 includes a temperature sensor for detecting the temperature of the atmospheric air (atmospheric temperature), for example. In the present embodiment, the gas temperature is regarded as atmospheric temperature. The temperature sensor includes, for example, a thermistor and a peripheral circuit thereof. The gas cloud temperature detection unit 3 outputs the detected gas temperature (the atmospheric temperature in the present embodiment) to the control processing unit 4.

The input unit 5 is a device connected to the control processing unit 4 and which inputs various commands such as a command instructing start of a detection operation to detect the leaked gas, and various data necessary to execute detection of the leaked gas such as an input of an identifier of the target area to the leaked gas detection device D. The input unit 5 is, for example, a plurality of input switches in which predetermined functions are allocated, a keyboard, or a mouse. The display unit 6 is a device connected to the control processing unit 4 and which outputs the command and data input from the input unit 5, and the gas cloud, the concentration-thickness product, the reliability degree, and a risk degree to be described below of the leaked gas detected by the leaked gas detection device D according to control of the control processing unit 4. The display unit 6 is a display device such as a cathode ray tube (CRT) display, a liquid crystal display, or an organic electroluminescence (EL) display.

Note that a touch panel may be constituted by the input unit 5 and the display unit 6. In constituting the touch panel, the input unit 5 is a position input device that detects and inputs an operation position, such as a resistive film-type or a capacitive-type position input device. The touch panel is provided with the position input device on a display surface of the display device, and one or a plurality of input content candidates inputtable to the display device are displayed. When a user touches a display position where the input content to be input is displayed, the position is detected by the position input device, and the display content displayed at the detected position is input to the leaked gas detection device D as operation input content of the user. In such a touch panel, the user can easily intuitively understand the input operation. Therefore, the leaked gas detection device D that is easy to handle for the user is provided.

The IF unit 7 is a circuit connected to the control processing unit 4 and which inputs/outputs data to/from an external device according to the control of the control processing unit 4. The IF unit 7 is, for example, an RS-232C interface circuit in a serial communication system, an interface circuit using the Bluetooth (registered trademark) standard, an interface circuit that performs infrared data association (IrDA)-standard infrared communication, an interface circuit using the universal serial bus (USB) standard, or the like. Further, the IF unit 7 is a communication card or the like that communicates by wired or wireless means, and may communicate with an external device such as a server device via a communication network such as an Ethernet environment (Ethernet is registered trademark).

The storage unit 8 is a circuit connected to the control processing unit 4 and which stores various predetermined programs and data according to the control of the control processing unit 4. The various predetermined programs include control processing programs such as a control program for controlling each unit of the leaked gas detection device D according to the function of each unit, a gas cloud processing program for extracting the gas cloud image area of the gas cloud formed with the leaked gas on the basis of the infrared image of the target area generated in the infrared imaging unit 1, a concentration-thickness product processing program for obtaining the concentration-thickness product of the gas cloud, a reliability degree processing program for obtaining a reliability degree that is an index representing the degree of reliability on the basis of the background temperature in the gas cloud image area extracted by the gas cloud processing program and the gas temperature detected in the gas cloud temperature detection unit 3, a risk degree processing program for obtaining a risk degree that is an index representing the degree of risk in toxicity, explosiveness, and the like, with respect to the concentration-thickness product of the gas cloud on the basis of the concentration-thickness product of the gas cloud obtained by the concentration-thickness product processing program, and a display processing program for displaying, on the display unit 6, the visible image of the target area generated in the visible imaging unit 2, the gas cloud image area extracted by the gas cloud processing program, the concentration-thickness product of the gas cloud obtained by the concentration-thickness product processing program, the reliability degree obtained by the reliability degree processing program, and the risk degree obtained by the risk processing program. The various predetermined data include data necessary to execute each program, and the like. The storage unit 8 includes, for example, a read only memory (ROM) that is a nonvolatile storage element, an electrically erasable programmable read only memory (EEPROM) that is a rewritable nonvolatile storage element, and the like. The storage unit 8 includes a random access memory (RAM) that serves as so-called a working memory of the control processing unit 4, which stores data and the like generated during the execution of the predetermined programs. Note that the storage unit 8 may include a hard disk having a relatively large storage capacity.

The control processing unit 4 is a circuit for controlling each unit of the leaked gas detection device D according to the function of each unit, and obtaining and displaying the concentration-thickness product, the reliability degree, and the risk degree in the gas cloud formed with the leaked gas. The control processing unit 4 includes, for example, a central processing unit (CPU) and a peripheral circuit thereof. In the control processing unit 4, a control unit 41, a gas cloud processing unit 42, a concentration-thickness product processing unit 43, a reliability degree processing unit 44, a risk degree processing unit 45, and a display processing unit 46 are functionally configured by execution of the control processing program.

The control unit 41 is for controlling each unit of the leaked gas detection device D according to the function of each unit.

The gas cloud processing unit 42 extracts the gas cloud image area of the gas cloud formed with the leaked gas on the basis of the infrared image of the target area generated in the infrared imaging unit 1.

Here, for example, as illustrated in FIG. 2, the leaked gas detection device D in the present embodiment is fixedly arranged to cause a capturing direction of the infrared imaging unit 1 and a capturing direction of the visible imaging unit 2 to face the target area so that the infrared image and the visible image in the target area can be respectively imaged by the infrared imaging unit 1 and the visible imaging unit 2. The infrared imaging unit 1 arranged in this manner images infrared rays (background radiation infrared rays and background emission infrared rays) radiated (emitted) by an individual object (background object) OB existing in the target area. As illustrated in FIG. 2, when a gas is leaked from a gas storage PY such as piping, and a gas cloud GS of the leaked gas exists between the infrared imaging unit 1 and the background object, the background radiation infrared rays reach the infrared imaging unit 1 via the gas cloud GS. The gas cloud GS absorbs a part of the background radiation infrared rays at a wavelength of an absorption line specific to the gas, and radiates infrared rays according to the temperature of the gas cloud GS itself. An amount of absorption with respect to the background radiation infrared rays depends on the concentration of the gas cloud GS, and then depends on the thickness of the gas cloud GS, and therefore depends on the concentration-thickness product of the gas cloud GS. Therefore, in the infrared image of the target area imaged and generated by the infrared imaging unit 1, a luminance value of a partial image via the gas cloud GS is different from a luminance value of a partial image without via the gas cloud GS. Therefore, the gas cloud processing unit 42 can extract the gas cloud image area of the gas cloud GS by extracting an area of pixels having a variation amount of the luminance value per unit time, which is equal to or less than a preset predetermined determination threshold Dth from the infrared image of the target area, for example.

The concentration-thickness product processing unit 43 obtains the concentration-thickness product of the gas cloud. In the present embodiment, the concentration-thickness product processing unit 43 obtains the concentration-thickness product of the gas cloud on the basis of the infrared image of the gas cloud image area extracted in the gas cloud processing unit 42 by using the technique disclosed in Patent Literature 1 described above, for example.

Further, as described above, since the gas cloud GS absorbs a part of the background radiation infrared rays at the wavelength of the absorption line specific to the gas, and radiates infrared rays according to the temperature of the gas cloud GS itself, an amount of infrared rays P observed in the infrared imaging unit 1 is expressed by the following equation 2 and can be rewritten as the following equation 3.

$$P=\int [\tau_g(\lambda,ct)B(T_{back},\lambda)+(1-\tau_g(\lambda,ct))B(T_g,\lambda)]d\lambda \quad (2)$$

$$P=\int [B(T_g,\lambda)+\tau_g(\lambda,ct)\{B(T_{back},\lambda)-B(T_g,\lambda)\}]d\lambda \quad (3)$$

Here, $\tau_g(\lambda, ct)$ is the absorption rate of the gas and is a function of the wavelength $\lambda$ and the concentration-thickness product ct, and therefore $(1-\tau_g(\lambda, ct))$ is the emissivity of the gas. $B(T_{back}, \lambda)$ is the amount of infrared rays (the amount of background radiation infrared rays) radiated (emitted) by the background and is a function of the background temperature $T_{back}$ and wavelength $\lambda$. $B(T_g, \lambda)$ is the amount of infrared rays (the amount of gas radiation infrared rays) radiated (emitted) by the gas of the gas cloud GS and is a function of the gas temperature $T_g$ and wavelength $\lambda$. Functional forms (shapes of graphs of the functions) in the functions $\tau_g(\lambda, ct)$, $B(T_{back}, \lambda)$, and $B(T_g, \lambda)$ are known in advance. In one example, the transmittance $\tau$ with respect to the wavelength $\lambda$ in methane gas is the characteristic curve illustrated in FIG. 3, and the spectral radiance with respect to the wavelength $\lambda$ in the methane gas is the characteristic curve illustrated in FIG. 4 at the temperature of 27° C. The amount of gas radiation infrared rays is obtained on the basis of the spectral radiance. Further, the amount of background radiation infrared rays is obtained on the basis of black body emission, regarding the background object as a black body. The integral $\int$ of each of the equations 2 and 3 is executed over a wavelength range of observed infrared rays.

The leaked gas detection device D obtains the amount of infrared rays P, the background temperature $T_{back}$, and the gas temperature $T_g$, and the concentration-thickness product processing unit 43 may assign the value of the concentration-thickness product ct in the equation 2 and obtain the concentration-thickness product ct by which both sides of the equation 2 become equal as the concentration-thickness product ct of the gas cloud GS, or the concentration-thickness product processing unit 43 may assign the value of the concentration-thickness product ct in the equation 3 and obtain the concentration-thickness product ct by which both sides of the equation 3 become equal as the concentration-thickness product ct of the gas cloud GS.

Note that the background temperature $T_{back}$ may be obtained on the basis of the luminance value of the image in the vicinity of the gas cloud image area in the target area and outside the gas cloud image area (out-of-area luminance value), or may be obtained by mounting a bandpass filter having an infrared wavelength range not including the wavelength of the absorption line as a transmission wavelength band to the infrared imaging unit 1, and obtaining the background temperature $T_{back}$ on the basis of a luminance value (area luminance value) of an area corresponding to the gas cloud image area in an infrared image of the target area obtained by the infrared imaging unit 1 via the bandpass filter. More specifically, a correspondence relationship (first conversion temperature correspondence relationship) between the out-of-area luminance value of the infrared image and the temperature (background temperature $T_{back}$) is stored in the storage unit 8 in advance as one of the various predetermined data, and the leaked gas detection device D obtains the background temperature $T_{back}$ corresponding to the out-of-area luminance value of the image outside the gas cloud image area from the first conversion temperature correspondence relationship by the control processing unit 4. Alternatively, a correspondence relationship (second conversion temperature correspondence relationship) between the area luminance value of the infrared image and the temperature (background temperature $T_{back}$) is stored in advance in the storage unit 8 as one of the various predetermined data, and the leaked gas detection device D obtains the background temperature $T_{back}$ corresponding to the area luminance value of the area corresponding to the gas cloud image area from the second conversion temperature correspondence relationship by the control processing unit 4.

In the present embodiment, the concentration-thickness product processing unit 43 respectively obtains the concentration-thickness products of the gas cloud at a plurality of points in the gas cloud.

The reliability degree processing unit 44 obtains the reliability degree that is an index representing the degree of reliability with respect to the concentration-thickness product of the gas cloud obtained in the concentration-thickness product processing unit 43 on the basis of the background temperature in the gas cloud image area extracted in the gas cloud processing unit 42 and the gas temperature detected in the gas cloud temperature detection unit 3.

Here, as described above, an error included in the concentration-thickness product obtained by the concentration-thickness product processing unit 43 depends on a difference between the background temperature and the gas temperature, and is larger as the difference between the background temperature and the gas temperature is smaller, as can be seen from FIG. 5. FIG. 5 illustrates an error (concentration-thickness product error) given to the concentration-thickness product by an error (gas temperature error) included in the measured gas temperature by simulation (numerical calculation experiment). The horizontal axis in FIG. 5 represents the gas temperature error expressed in ° C., and the vertical axis represents the error rate of the concentration-thickness product expressed in %. The solid line α1 indicates the error rate of the concentration-thickness product when the difference between the background temperature and the gas temperature is 2° C., the alternate long and short dashed line α2 indicates the error rate of the concentration-thickness product when the difference between the background temperature and the gas temperature is 5° C., and the broken line α3 indicates the error rate of the concentration-thickness product when the difference between the background temperature and the gas temperature is 10° C. Even in any case of the gas temperature error (no matter where on the horizontal axis), the error rate of the concentration-thickness product is larger, in its absolute values, in the difference between the background temperature and the gas temperature of 5° C. than the difference of 10° C., and is larger in the difference of 2° C. than the difference of 5° C. Therefore, as described above, the error included in the concentration-thickness product obtained by the concentration-thickness product processing unit 43 depends on the difference between the background temperature and the gas temperature, and is larger as the difference between the background temperature and the gas temperature is smaller.

More specifically, under the result illustrated in FIG. 5, a correspondence relationship between the background temperature and the gas temperature (reliability degree correspondence relationship) is stored in advance in the storage unit 8 as one of the various predetermined data, and the reliability degree processing unit 44 obtains a difference Sub between the background temperature $T_{back}$ in the gas cloud image area extracted in the gas cloud processing unit 42 and the gas temperature $T_g$ detected in the gas cloud temperature detection unit 3, by the above-described technique, and obtains the reliability degree with respect to the obtained difference Sub from the reliability degree correspondence relationship. For example, in the reliability degree correspondence relationship, a "small reliability degree" or "50% or less" in which the reliability is low is associated with the difference Sub equal to or less than a preset first reliability degree determination threshold Tth1, an "intermediate reliability degree" or "50% to 80%" in which the reliability is intermediate is associated with the difference Sub exceeding the first reliability degree determination threshold Tth1 and equal to or lower than a preset second reliability degree determination threshold Tth2, and a "large reliability degree" or "80% or more" in which the reliability is high is associated with the difference Sub exceeding the second reliability degree determination threshold Tth2.

Then, the reliability degree processing unit 44 respectively obtains the reliability degrees for the plurality of concentration-thickness products obtained at the plurality of points in the gas cloud, corresponding to the processing of the concentration-thickness product processing unit 43.

The risk degree processing unit 45 obtains the risk degree that is an index representing the degree of risk with respect to the concentration-thickness product of the gas cloud obtained by the concentration-thickness product processing unit 43. More specifically, a correspondence relationship (risk degree correspondence relationship) between the concentration-thickness product of the gas cloud and the risk degree is stored in advance in the storage unit 8 as one of the various predetermined data, and the risk degree processing unit 45 obtains the risk degree with respect to the concentration-thickness product ct of the gas cloud obtained in the concentration-thickness product processing unit 43 from the risk degree correspondence relationship. For example, in the risk degree correspondence relationship, a "small risk degree" in which the risk is low is associated with the concentration-thickness product ct equal to or less than a preset first risk degree determination threshold Gth1, an "intermediate risk degree" in which the risk is intermediate is associated with the concentration-thickness product ct exceeding the first risk degree determination threshold Gth1 and equal to or less than a preset second risk degree determination threshold Gth2, and a "large risk degree" in which the risk is high is associated with the concentration-thickness product ct exceeding the second risk degree determination threshold Gth2.

Then, the risk degree processing unit 45 respectively obtains the risk degrees for the plurality of concentration-thickness products obtained at the plurality of points in the gas cloud, corresponding to the processing of the concentration-thickness product processing unit 43.

The display processing unit 46 displays the visible image of the target area generated in the visible imaging unit 2, the gas cloud image area extracted in the gas cloud processing unit 42, the concentration-thickness product of the gas cloud obtained in the concentration-thickness product processing unit 43, the reliability degree obtained in the reliability degree processing unit 44, and the risk degree obtained in the risk degree processing unit 45 on the display unit 6. More specifically, the display processing unit 46 superimposes the gas cloud image area extracted in the gas cloud processing unit 42 on the visible image of the target area generated in the visible imaging unit 2 and displays the superimposed image on the display unit 6, and displays the concentration-thickness product, the reliability degree, and the risk degree on the display unit 6 in association with the gas cloud image area. Then, in the present embodiment, for each of the plurality of points in the gas cloud, the display processing unit 46 fills an area corresponding to the point with a predetermined color and displays the area on the display unit 6, and does not display the concentration-thickness product, the reliability degree, and the risk degree corresponding to the point on the display unit 6, when the reliability degree corresponding to the point is equal to or less than a predetermined first threshold Th1.

In the above description, the infrared imaging unit 1, the visible imaging unit 2, the gas cloud temperature detection unit 3, the control processing unit 4, the input unit 5, the display unit 6, the IF unit 7, and the storage unit 8 may be put together as one unit to constitute the leaked gas detection device D. In this case, the infrared imaging unit 1 corresponds to an example of an infrared image acquisition unit that acquires the infrared image of the target area, and the gas cloud temperature detection unit 3 corresponds to an example of a gas cloud temperature acquisition unit that acquires the gas temperature of the gas cloud. Alternatively, the infrared imaging unit 1, the visible imaging unit 2, and the gas cloud temperature detection unit 3 may be put together as one unit to constitute a sensor unit, and the control processing unit 4, the input unit 5, the display unit 6, the IF unit 7, and the storage unit 8 may be put together as one unit to constitute a main unit, and the leaked gas detection device D may be constituted by including the sensor unit and the main unit communicatively connected by wired or wireless means. In this case, the IF unit 7 corresponds to another example of the infrared image acquisition unit that acquires the infrared image of the target area, and further corresponds to another example of the gas cloud temperature acquisition unit that acquires the gas temperature of the gas cloud. Then, in these cases, to enable monitoring at a remote place, the display unit 6 may be further separated and arranged at a remote place in a state of being communicatively connected by wired or wireless means.

Figure 6:
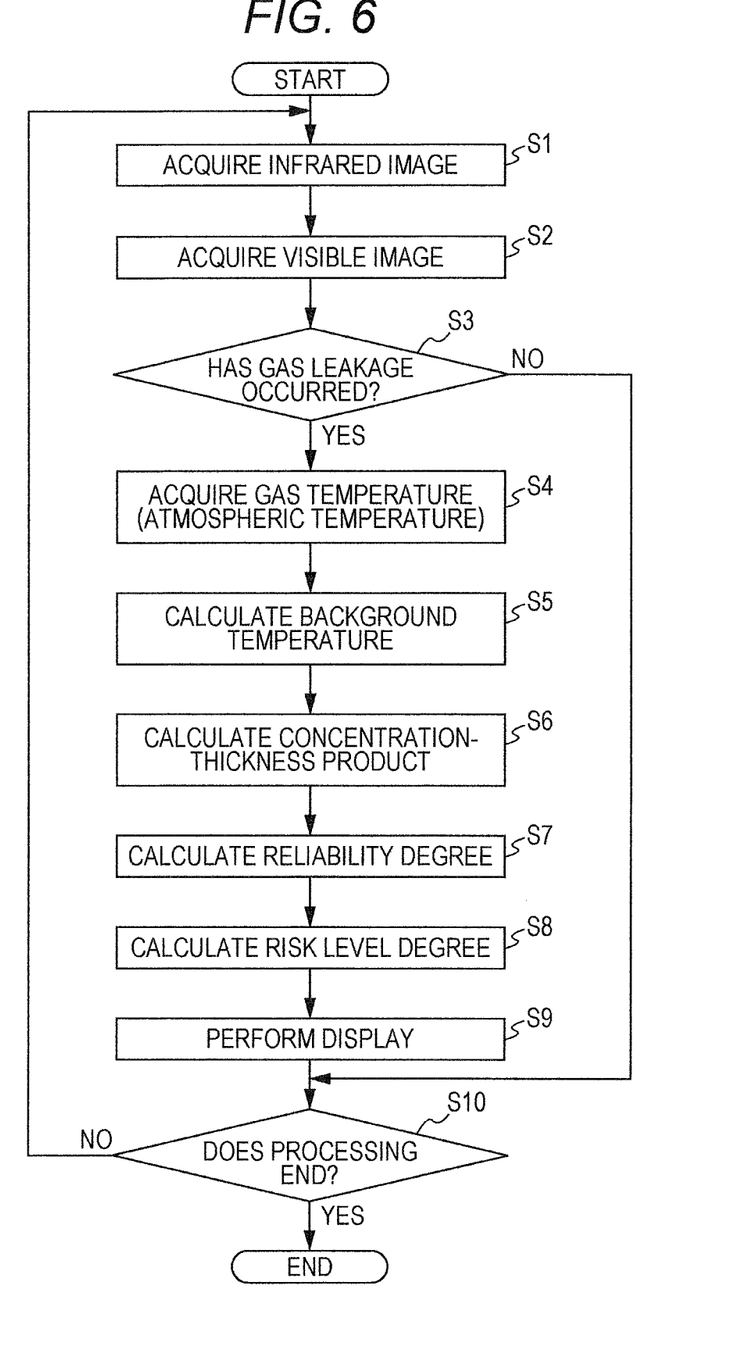
FIG. 6 is a flowchart illustrating an operation of the leaked gas detection device.
Figure 7:
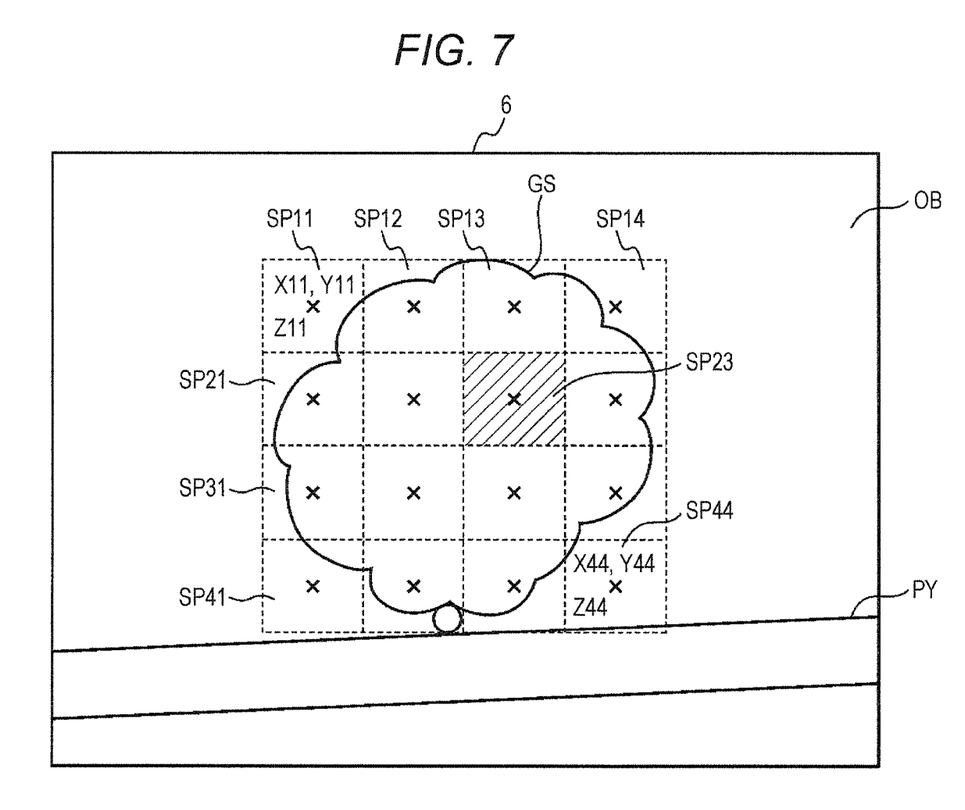
FIG. 7 is a schematic diagram for describing a display screen of the leaked gas detection device.

Next, an operation of the present embodiment will be described. FIG. 6 is a flowchart illustrating an operation of the leaked gas detection device in the embodiment. FIG. 7 is a schematic diagram for describing a display screen of the leaked gas detection device in the embodiment.

The leaked gas detection device D is disposed to cause the capturing direction of the infrared imaging unit 1 and the capturing direction of the visible imaging unit 2 to face the target area, and when a power switch (not illustrated) is turned on by the user (operator), the control processing unit 4 executes initialization of necessary units, and by execution of the control processing program, the control unit 41, the gas cloud processing unit 42, the concentration-thickness product processing unit 43, the reliability degree processing unit 44, the risk degree processing unit 45, and the display processing unit 46 are functionally configured in the control processing unit 4. When the start of the detection operation is input and instructed from the input unit 5 by the user, the detection operation of the leaked gas is started for the target area.

More specifically, in FIG. 6, first, the leaked gas detection device D images the target area by the infrared imaging unit 1 in an infrared manner, and generates and acquires the infrared image of the target area. The infrared image (image data of the infrared image) of the target area is output from the infrared imaging unit 1 to the control processing unit 4 (S1).

Next, the leaked gas detection device D images the target area by the visible imaging unit 2 in a visible manner, and generates and acquires the visible image of the target area. The visible image (image data of the visible image) of the target area is output from the visible imaging unit 2 to the control processing unit 4 (S2).

Next, the leaked gas detection device D determines whether gas leakage has occurred by the control processing unit 4 (S3). That is, the leaked gas detection device D determines, by the control processing unit 4, whether gas leakage has occurred by determining the presence or absence of the gas cloud GS of the leaked gas. More specifically, the control processing unit 4 extracts, by the gas cloud processing unit 42, the gas cloud image area of the gas cloud GS formed with the leaked gas on the basis of the infrared image of the target area generated in the infrared imaging unit 1. As a result, when the gas cloud image area is not extracted (No), the control processing unit 4 determines that the gas cloud GS of the leaked gas has not occurred, that is, the gas leakage has not occurred, and execute the processing S10 described below. On the other hand, when the gas cloud image area is extracted (Yes), the control processing unit 4 determines that the gas cloud GS of the leaked gas has occurred, that is, the gas leakage has occurred, and execute the next processing S4.

In the processing S4, the leaked gas detection device D detects and acquires the gas temperature (the atmospheric temperature in the present embodiment) $T_g$ of the gas cloud GS by the gas cloud temperature detection unit 3. The gas temperature (atmospheric temperature) $T_g$ is output from the gas cloud temperature detection unit 3 to the control processing unit 4.

Next, the leaked gas detection device D obtains, by the control processing unit 4, the background temperature $T_{back}$ on the basis of the infrared image of the target area generated in the infrared imaging unit 1 (S5). More specifically, for example, the control processing unit 4 obtains an out-of-area luminance value of an image in the vicinity of the gas cloud image area and outside the gas cloud image area, and obtains the background temperature $T_{back}$ corresponding to this out-of-area luminance value from the first conversion temperature correspondence relationship stored in advance in the storage unit 8. Further, for example, the control processing unit 4 may obtain an area luminance value of an area corresponding to the gas cloud image area in the infrared image of the target area obtained by the infrared imaging unit 1 via a bandpass filter having an infrared wavelength range without including a wavelength of the absorption line as the transmission wavelength band, and obtains the background temperature $T_{back}$ corresponding to the area luminance value from the second conversion temperature correspondence relationship stored in advance in the storage unit 8.

Note that the processing S4 and the processing S5 described above may be switched in order and executed, or may be concurrently executed (by parallel processing).

Next, the leaked gas detection device D obtains, by the concentration-thickness product processing unit 43, the concentration-thickness product ct of the gas cloud GS on the basis of the infrared image of the gas cloud image area extracted in the gas cloud processing unit 42 (S6). In the present embodiment, the concentration-thickness product processing unit 43 obtains the concentration-thickness products ct of the gas cloud GS at a plurality of points in the gas cloud GS. Therefore, in the above-described processing S5, the control processing unit 4 may obtain the background temperature $T_{back}$ for each of the plurality of points in the gas cloud GS, corresponding to the processing of the concentration-thickness product processing unit 43. Alternatively, each background temperature $T_{back}$ in each of the plurality of points in the gas cloud may be represented by one background temperature $T_{back}$ obtained in the above-described processing S5.

Next, the leaked gas detection device D obtains, by the reliability degree processing unit 44, the reliability degree with respect to the concentration-thickness product of the gas cloud GS obtained in the concentration-thickness product processing unit 43 on the basis of the background temperature $T_{back}$ in the gas cloud image area extracted in the gas cloud processing unit 42 and the gas temperature $T_g$ detected in the gas cloud temperature detection unit 3 (S7). More specifically, in the present embodiment, the reliability degree processing unit 44 calculates the difference Sub between the background temperature $T_{back}$ in the gas cloud image area extracted in the gas cloud processing unit 42 and the gas temperature $T_g$ detected in the gas cloud temperature detection unit 3, and obtains the reliability degree with respect to the obtained difference Sub from the reliability degree correspondence relationship. Then, in the present embodiment, the reliability degree processing unit 44 respectively obtains the reliability degrees for the plurality of concentration-thickness products ct obtained at the plurality of points in the gas cloud GS, corresponding to the processing S6 of the concentration-thickness product processing unit 43.

Next, the leaked gas detection device D obtains, by the risk degree processing unit 45, the risk degree for the concentration-thickness product ct of the gas cloud GS obtained in the concentration-thickness product processing unit 43 (S8). More specifically, in the present embodiment, the risk degree processing unit 45 obtains the risk degree for the concentration-thickness product ct of the gas cloud GS obtained in the concentration-thickness product processing unit 43 from the risk degree correspondence relationship. Then, in the present embodiment, the risk degree processing unit 45 respectively obtains the risk degrees for the plurality of concentration-thickness products ct obtained at the plurality of points in the gas cloud GS, corresponding to the processing S6 of the concentration-thickness product processing unit 43.

Next, the leaked gas detection device D displays, by the display processing unit 46, the visible image of the target area generated in the visible imaging unit 2, the gas cloud image area extracted in the gas cloud processing unit 42, the concentration-thickness product ct of the gas cloud GS obtained in the concentration-thickness product processing unit 43, the reliability degree obtained in the reliability degree processing unit 44, and the risk degree obtained in the risk degree processing unit 45 on the display unit 6. More specifically, the display processing unit 46 positions and superimposes the gas cloud image area extracted in the gas cloud processing unit 42 on the visible image of the target area generated in the visible imaging unit 2 and displays the superimposed image on the display unit 6, and displays the concentration-thickness product ct, the reliability degree, and the risk degree on the display unit 6 in association with the gas cloud image area. Then, in the present embodiment, for each of the plurality of points in the gas cloud GS, the display processing unit 46 fills an area corresponding to the point with a predetermined color and displays the area on the display unit 6, and does not display the concentration-thickness product ct, the reliability degree, and the risk degree corresponding to the point on the display unit 6, when the reliability degree corresponding to the point is equal to or less than the predetermined first threshold Th1.

In an example, as illustrated in FIG. 7, for example, these pieces of information are displayed on the display unit 6. More specifically, the gas cloud image area extracted in the above-described processing S1 to S3 is divided into a plurality of areas as the plurality of points in the gas cloud GS. For example, as illustrated in FIG. 7, a rectangular area including the gas cloud image area, preferably, a rectangular area inscribing the gas cloud image area is set, and the set rectangular is divided into a plurality of divided areas having the equal size in a two-dimensional matrix manner. In the example illustrated in FIG. 7, the rectangular area inscribing the gas cloud image area is divided into 16 divided areas SP11 to SP44 (SP11 to SP14, SP21 to SP24, SP31 to SP34, and SP41 to SP44) arrayed in a two-dimensional matrix manner of 4 rows by 4 columns. Note that the number of divided areas may be any another arbitrary number. For each of these 16 divided areas SP11 to SP44, the concentration-thickness product ct, the reliability degree, and the risk degree of the divided area SP are obtained by the processing S4 to S8. The luminance value of the divided area SP may be, for example, an average value of luminance values of pixels included in the divided area SP, may be, for example, a median value of the luminance values of the pixels included in the divided area SP, or may be, for example, a luminance value of the pixel in the central position of the divided area SP. The average value may be a simple average or may be a weighted average. In the case of the weighted average, the weight is a function of a pixel position, and gradually becomes a larger value from a periphery of the divided area to the central position. In processing S9, as illustrated in FIG. 7, the display processing unit 46 positions and superimposes the gas cloud image area of the gas cloud GS extracted in the gas cloud processing unit 42 on the visible image of the target area generated in the visible imaging unit 2, and displays the superimposed image on the display unit 6. Then, as illustrated in FIG. 7, the display processing unit 46 displays the rectangular areas and its divided areas SP11 to SP44 on the display unit 6 with broken lines at their boundary lines, and displays concentration-thickness products X11 to X44 (X11 to X14, X21 to X24, X31 to X34, and X41 to X44), reliability degrees Y11 to Y44 (Y11 to Y14, Y21 to Y24, Y31 to Y34, and Y41 to Y44), and risk degrees Z11 to Z44 (Z11 to Z14, Z21 to Z24, Z31 to Z34, and Z41 to Z44) of the divided areas SP11 to SP44, in the divided areas SP11 to SP44, respectively. As a result, the concentration-thickness product X, the reliability degree Y, and the risk degree Z are displayed on the display unit 6, for each divided area. In FIG. 7, since the drawing becomes complicated and difficult to see, the concentration-thickness product X, the reliability degree Y, and the risk degree Z are illustrated in the first-row and first-column divided area and the fourth-row and fourth-column divided area. However, illustration of the concentration-thickness product X, the reliability degree Y, and the risk degree Z is omitted in other divided areas. In the example illustrated in FIG. 7, since the reliability degree of the second-row and third-column divided area is equal to or less than the predetermined first threshold Th1, the second-row and third-column divided area is filled with a predetermined color (for example, yellow, orange, or purple) and displayed, and the concentration-thickness product X, the reliability degree Y, and the risk degree Z are not displayed in the second-row and third-column divided area.

Referring back to FIG. 6, in processing S10, the leaked gas detection device D determines, by the control processing unit 4, whether termination of the detection operation by the user has been received in the input unit 5, and terminates the processing when the termination of the detection operation has been received in the input unit 5 (Yes), and returns the processing to processing S1 when the termination of the detection operation has not been received in the input unit 5 (No).

As described above, in the leaked gas detection device D in the present embodiment and a leaked gas detection method implemented therein, the reliability degree with respect to the obtained concentration-thickness product of the gas cloud is obtained on the basis of the background temperature of the gas cloud image area in the infrared image and the gas temperature, which correlate with the background temperature, from the newly found knowledge, while obtaining the concentration-thickness product without performing correction. Therefore, the above-described leaked gas detection device D and the leaked gas detection method enable the user to determine the degree of reliability of the concentration-thickness product by reference to the reliability degree while prioritizing the real-time properties. Therefore, for example, in the case of the concentration-thickness product that needs to be coped, the user can determine that the concentration-thickness product should be immediately coped in the case where the reliability degree has a dependable high value, whereas measures to obtain the concentration-thickness product with a high reliability degree can be conducted, such re-detection or detection by shifting the position where the concentration-thickness product is obtained, in the case where the reliability degree has an undependable low value.

In the leaked gas detection device D and the leaked gas detection method, for each of the plurality of points, the concentration-thickness product and the reliability degree corresponding to each of the plurality of points are obtained, and when the reliability degree corresponding to the point is equal to or less than the predetermined first threshold Th1, an area corresponding to the point is filled with a predetermined color and displayed on the display unit 6, and the concentration-thickness product and the reliability degree corresponding to the point are not displayed on the display unit 6. Therefore, the user does not refer to the concentration-thickness product with a low reliability degree when the reliability degree is equal to or less than the first threshold Th1, and false recognition of the concentration-thickness product of the leaked gas caused in the user by reference to the concentration-thickness product with a low reliability degree can be decreased.

In the leaked gas detection device D and the leaked gas detection method, the gas cloud temperature detection unit 3 is constituted by a temperature sensor that detects the temperature of the atmospheric air. Therefore, the gas temperature can be more easily detected.

Note that, in the above-described embodiment, the leaked gas detection device D may further include, as illustrated by the broken line in FIG. 1, an ambient reliability degree determination processing unit 47 that determines a point having the highest reliability degree in points around the point when the reliability degree corresponding to the point is equal to or less than a predetermined second threshold Th2, for each of the plurality of points in the gas cloud. The second threshold Th2 may be the same value as the first threshold Th1 or may be a different value from the first threshold Th1.

Figure 8:
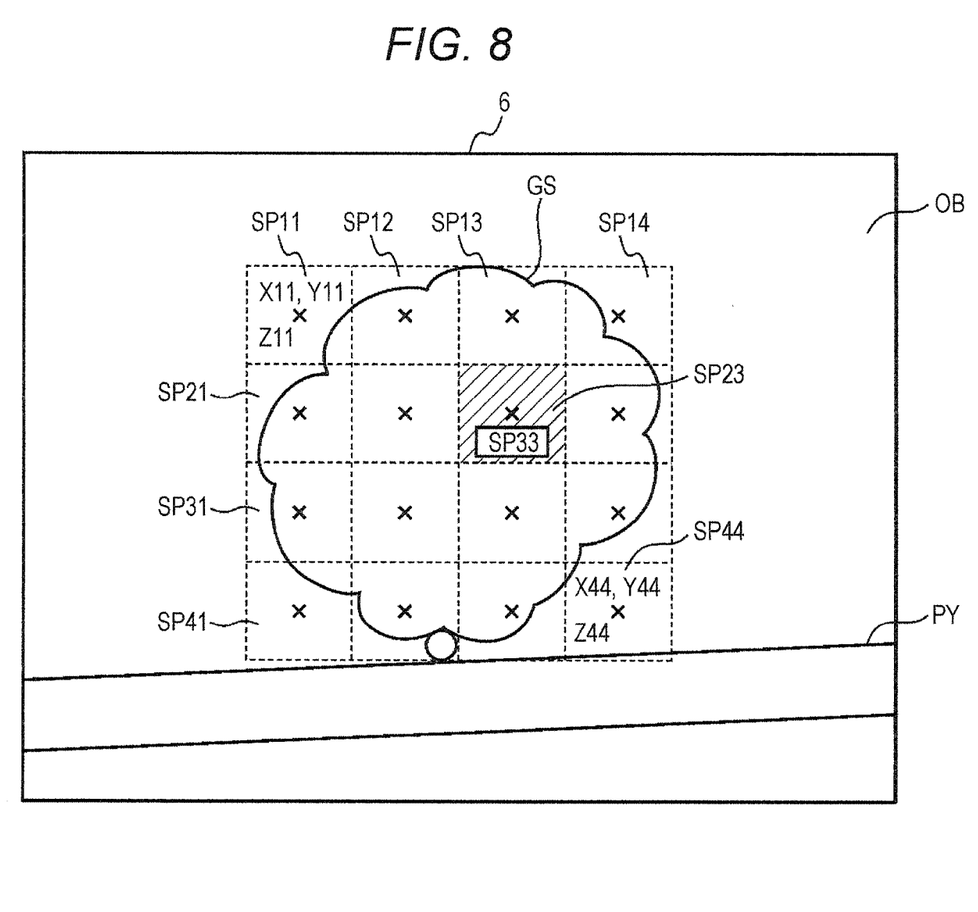
FIG. 8 is a schematic diagram for describing a display screen of a leaked gas detection device in a modification.

FIG. 8 is a schematic diagram for describing a display screen of a leaked gas detection device in a modification. For example, in the example illustrated in FIG. 7 described above, in the case where the reliability degree of the second-row and third-column division area SP23 is equal to or less than the predetermined second threshold Th2, the ambient reliability degree determination processing unit 47 obtains the divided area SP having the highest reliability degree in the periphery of the second-row and third-column division area SP23, that is, in the eight divided areas SP12 to SP14, SP22, SP24, and SP32 to SP34, and displays the obtained divided area SP having the highest reliability degree on the display unit 6 in association with the second-row and third-column division area SP23. For example, in the case where the obtained divided area SP having the highest reliability degree is the third-row and third-column divided area SP33, the name "SP33" representing the third-row and third-column divided area SP33 is displayed in the filled second-row and third-column divided area SP23, as illustrated in FIG. 8. In the case where a plurality of divided areas SP having the highest reliability degree exists, all of the divided areas SP are written together.

In such a leaked gas detection device D, for each of the plurality of points, the concentration-thickness product and the reliability degree corresponding to the point are obtained, and when the reliability degree corresponding to the point is equal to or less than the predetermined second threshold Th2, the point having the highest reliability degree in points around the point is determined. Therefore, the user can refer to the concentration-thickness product at the point having the highest reliability degree in ambient points, in place of the concentration-thickness product having a low reliability degree when the reliability degree is equal to or less than the second threshold Th2.

Further, in the above-described embodiment, the reliability degree is displayed on the display unit 6 separately from the concentration-thickness product. However, the display processing unit 46 may display the reliability degree in the display color of the concentration-thickness product. For example, the concentration-thickness product is displayed in red when the reliability degree is equal to or less than 50%, the concentration-thickness product is displayed in yellow when the reliability degree is 50% to 80%, and the concentration-thickness product is displayed in green when the reliability degree is equal to or more than 80%. Such a leaked gas detection device D displays the reliability degree in the display color of the concentration-thickness product. Therefore, the reliability degree can be intuitively visually recognized, as compared with display with a numerical value.

Further, in the above embodiment, in the case where the reliability degree obtained in the reliability degree processing unit 44 is equal to or less than a predetermined third threshold Th3, the concentration-thickness product processing unit 43 may obtain the concentration-thickness product of the gas cloud again after passage of a predetermined time (for example, after 30 seconds, after 1 minute, after 3 minutes, after 5 minutes, or after 10 minutes), and the display processing unit 46 may display the re-obtained concentration-thickness product of the gas cloud on the display unit 6. The third threshold Th3 may be the same value as the first threshold Th1 or may be a different value from the first threshold Th1. The third threshold Th3 may be the same value as the second threshold Th2 or may be a different value from the second threshold Th2. Such a leaked gas detection device D obtains the concentration-thickness product again, and thus enables the user to refer to the concentration-thickness product with a higher reliability degree than the third threshold Th3.

Although the present specification discloses the techniques of various aspects as described above, the main technologies among them are summarized below.

A leaked gas detection device according to one aspect includes an infrared image acquisition unit that acquires an infrared image of a target area, a gas cloud processing unit that extracts a gas cloud image area of a gas cloud formed with a leaked gas on the basis of the infrared image of the target area acquired in the infrared image acquisition unit, a gas cloud temperature acquisition unit that acquires a gas temperature of the gas cloud, a concentration-thickness product processing unit that obtains a concentration-thickness product of the gas cloud, and a reliability degree processing unit that obtains a reliability degree that is an index representing the degree of reliability with respect to the concentration-thickness product of the gas cloud obtained in the concentration-thickness product processing unit on the basis of a background temperature in the gas cloud area extracted in the gas cloud processing unit and the gas temperature acquired in the gas cloud temperature acquisition unit. Preferably, in the above-described leaked gas detection device, the infrared image acquisition unit is an interface unit that receives an input of data from an external device, and the interface unit receives an input of the infrared image of the target area from an infrared imaging unit that images the target area in an infrared manner to generate the infrared image of the target area as the external device. Preferably, in the above-described leaked gas detection device, the infrared image acquisition unit is an infrared imaging unit that images the target area in an infrared manner to generate the infrared image of the garget area. Preferably, in the above-described leaked gas detection device, the gas cloud temperature acquisition unit is an interface that receives an input of data from an external device, and the interface unit receives an input of the gas temperature of the gas cloud from a gas cloud temperature detection unit that detects the gas temperature of the gas cloud. Preferably, in the above-described leaked gas detection device, the gas cloud temperature acquisition unit is a gas cloud temperature detection unit that detects the gas temperature of the gas cloud.

As described above, an error included in the obtained concentration-thickness product depends on a difference between the background temperature and the gas temperature, and is larger as the difference between the background temperature and the gas temperature is smaller. In the above-described leaked gas detection device, the reliability degree with respect to the obtained concentration-thickness product of the gas cloud is obtained on the basis of the background temperature and the gas temperature from the newly found knowledge while obtaining the concentration-thickness product without performing correction. Therefore, the above-described leaked gas detection device enables the user to determine the degree of reliability of the concentration-thickness product by reference to the reliability degree while prioritizing the real-time properties.

In another aspect, the leaked gas detection device further includes a display processing unit that makes the gas cloud image area extracted in the gas cloud processing unit, the concentration-thickness product of the leaked gas obtained in the concentration-thickness product processing unit, and the reliability degree obtained in the reliability degree processing unit displayable on a display unit, wherein the concentration-thickness product processing unit respectively obtains the concentration-thickness products of the gas cloud at a plurality of points of the gas cloud on the basis of the infrared image of the target area acquired in the infrared image acquisition unit, the reliability degree processing unit obtains the reliability degree for the plurality of concentration-thickness products of the gas cloud respectively obtained at the plurality of points in the gas cloud, and the display processing unit displays an area corresponding to the point, filling the area with a predetermined color, on the display unit, and does not display the concentration-thickness product of the gas cloud and the reliability degree corresponding to the point on the display unit when the reliability degree corresponding to the point is equal to or less than a predetermined first threshold.

In such a leaked gas detection device, for each of the plurality of points, the concentration-thickness product and the reliability degree corresponding to the point are obtained, and when the reliability degree corresponding to the point is equal to or less than the predetermined first threshold, the area corresponding to the point is filled with the predetermined color and displayed on the display unit, and the concentration-thickness product and the reliability degree corresponding to the point are not displayed on the display unit. Therefore, the user does not refer to the concentration-thickness product with a low reliability degree when the reliability degree is equal to or less than the first threshold, and false recognition of the concentration-thickness product of the leaked gas caused in the user by reference to the concentration-thickness product with a low reliability degree can be decreased.

In another aspect, in the leaked gas detection device according, the concentration-thickness product processing unit respectively obtains the concentration-thickness products of the gas cloud at a plurality of points of the gas cloud on the basis of the infrared image of the target area acquired in the infrared image acquisition unit, and the reliability degree processing unit obtains the reliability degrees for the plurality of concentration-thickness products of the gas cloud respectively obtained at the plurality of points in the gas cloud, and the leaked gas detection device further includes an ambient reliability degree determination processing unit that determines, for each of the plurality of points in the gas cloud, a point having a highest reliability degree in points around the point when the reliability degree corresponding to the point is equal to or less than a predetermined second threshold. The second threshold may be the same value as the first threshold, or may be a different value from the first threshold.

In such a leaked gas detection device, for each of the plurality of points, the concentration-thickness product and the reliability degree corresponding to the point are obtained, and when the reliability degree corresponding to the point is equal to or less than the predetermined second threshold, the point having the highest reliability degree in points around the point is determined. Therefore, the user can refer to the concentration-thickness product at the point having the highest reliability degree in ambient points, in place of the concentration-thickness product having a low reliability degree when the reliability degree is equal to or less than the second threshold.

In another aspect, the leaked gas detection device further includes a display processing unit that makes the gas cloud image area extracted in the gas cloud processing unit, the concentration-thickness product of the leaked gas obtained in the concentration-thickness product processing unit, and the reliability degree obtained in the reliability degree processing unit displayable on a display unit, wherein the display processing unit displays the reliability degree in a display color of the concentration-thickness product.

Such a leaked gas detection device displays the reliability degree in the display color of the concentration-thickness product. Therefore, the reliability degree can be intuitively visually recognized, as compared with display with a numerical value.

In another aspect, in the leaked gas detection device, the concentration-thickness product processing unit obtains the concentration-thickness product of the gas cloud after passage of a predetermined time when the reliability degree obtained in the reliability degree processing unit is equal to or less than a predetermined third threshold. The third threshold may be the same value as the first threshold, or may be a different value from the first threshold. The third threshold may be the same value as the second threshold, or may be a different value from the second threshold.

Such a leaked gas detection device obtains the concentration-thickness product again, and thus enables the user to refer to the concentration-thickness product with a higher reliability degree than the third threshold.

In another aspect, in the leaked gas detection device, the gas cloud temperature acquisition unit is a temperature sensor that detects a temperature of atmospheric air.

In such a leaked gas detection device, the gas cloud temperature acquisition unit is constituted using the temperature sensor that detects the temperature of the atmospheric air, and thus the gas temperature can be more simply detected.

A leaked gas detection method according to another aspect includes an infrared image acquisition step of acquiring an infrared image of a target area, a gas cloud processing step of extracting a gas cloud image area of a gas cloud formed with a leaked gas on the basis of the infrared image of the target area acquired in the infrared image acquisition step, a gas cloud temperature acquisition step of acquiring a gas temperature of the gas cloud, a concentration-thickness product processing step of obtaining a concentration-thickness product of the gas cloud, and a reliability degree processing step of obtaining a reliability degree that is an index representing the degree of reliability with respect to the concentration-thickness product of the gas cloud obtained in the concentration-thickness product processing step on the basis of a background temperature in the gas cloud area extracted in the gas cloud processing step and the gas temperature acquired in the gas cloud temperature acquisition step.

In such a leaked gas detection method, the reliability degree with respect to the obtained concentration-thickness product of the gas cloud is obtained on the basis of the luminance value of the gas cloud image area in the infrared image and the gas temperature, which correlate with the background temperature, from the newly found knowledge, while obtaining the concentration-thickness product without performing correction. Therefore, the above-described leaked gas detection method enables the user to determine the degree of reliability of the concentration-thickness product by reference to the reliability degree while prioritizing the real-time properties.

This application is based on Japanese Patent Application No. 2015-212507 filed on Oct. 29, 2015, the contents of which are hereby incorporated herein by reference.

To express the present invention, while the present invention has been appropriately and fully described through the embodiments with reference to the drawings in the foregoing, it should be recognized that those skilled in the art can easily modify and/or improve the above-described embodiments. Therefore, it is construed that modified forms and improved forms are included in the scope of claims as long as the modified forms and improved forms implemented by those skilled in the art do not depart from the scope of claims described in the claims.

INDUSTRIAL APPLICABILITY

According to the present invention, a leaked gas detection device and a leaked gas detection method can be provided.

The invention claimed is:

1. A leaked gas detection device comprising:
an infrared image acquisitor that acquires an infrared image of a target area;
a hardware processor that extracts a gas cloud image area of a gas cloud formed with a leaked gas on the basis of the infrared image of the target area acquired in the infrared image acquisitor; and
a gas cloud temperature acquisitor that acquires a gas temperature of the gas cloud,
the hardware processor obtaining a concentration-thickness product of the gas cloud, and obtaining a reliability degree that is an index representing the degree of reliability with respect to the concentration-thickness product of the gas cloud obtained in the hardware processor on the basis of a background temperature in the gas cloud image area extracted in the hardware processor and the gas temperature acquired in the gas cloud temperature acquisitor.

2. The leaked gas detection device according to claim 1, wherein
the hardware processor makes the gas cloud image area extracted in the hardware processor, the concentration-thickness product of the leaked gas obtained in the hardware processor, and the reliability degree obtained in the hardware processor displayable on a display,
respectively obtains the concentration-thickness products of the gas cloud at a plurality of points of the gas cloud on the basis of the infrared image of the target area acquired in the infrared image acquisitor,
respectively obtains the reliability degrees for the plurality of concentration-thickness products of the gas cloud respectively obtained at the plurality of points in the gas cloud, and
displays, for each of the plurality of points in the gas cloud, an area corresponding to the point, filling the area with a predetermined color, on the display, and does not display the concentration-thickness product of the gas cloud and the reliability degree corresponding to the point on the display, when the reliability degree corresponding to the point is equal to or less than a predetermined first threshold.

3. The leaked gas detection device according to claim 2, wherein
the hardware processor obtains the concentration-thickness product of the gas cloud again after passage of a predetermined time when the reliability degree obtained in the hardware processor is equal to or less than a predetermined third threshold.

4. The leaked gas detection device according to claim 2, wherein
the gas cloud temperature acquisitor is a temperature sensor that detects a temperature of atmospheric air.

5. The leaked gas detection device according to claim 1, wherein
the hardware processor respectively obtains the concentration-thickness products of the gas cloud at a plurality of points of the gas cloud on the basis of the infrared image of the target area acquired in the infrared image acquisitor,
respectively obtains the reliability degrees for the plurality of concentration-thickness products of the gas cloud respectively obtained at the plurality of points in the gas cloud, and
determines, for each of the plurality of points in the gas cloud, a point having a highest reliability degree in points around the point when the reliability degree corresponding to the point is equal to or less than a predetermined second threshold.

6. The leaked gas detection device according to claim 5, wherein
the hardware processor obtains the concentration-thickness product of the gas cloud again after passage of a predetermined time when the reliability degree obtained in the hardware processor is equal to or less than a predetermined third threshold.

7. The leaked gas detection device according to claim 5, wherein
the gas cloud temperature acquisitor is a temperature sensor that detects a temperature of atmospheric air.

8. The leaked gas detection device according to claim 1, wherein
the hardware processor makes the gas cloud image area extracted in the hardware processor, the concentration-thickness product of the leaked gas obtained in the hardware processor, and the reliability degree obtained in the hardware processor displayable on a display, and
displays the reliability degree in a display color of the concentration-thickness product.

9. The leaked gas detection device according to claim 8, wherein
the hardware processor obtains the concentration-thickness product of the gas cloud again after passage of a predetermined time when the reliability degree obtained in the hardware processor is equal to or less than a predetermined third threshold.

10. The leaked gas detection device according to claim 8, wherein
the gas cloud temperature acquisitor is a temperature sensor that detects a temperature of atmospheric air.

11. The leaked gas detection device according to claim 1, wherein
the hardware processor obtains the concentration-thickness product of the gas cloud again after passage of a predetermined time when the reliability degree obtained in the hardware processor is equal to or less than a predetermined third threshold.

12. The leaked gas detection device according to claim 11, wherein
the gas cloud temperature acquisitor is a temperature sensor that detects a temperature of atmospheric air.

13. The leaked gas detection device according to claim 1, wherein
the gas cloud temperature acquisitor is a temperature sensor that detects a temperature of atmospheric air.

14. A leaked gas detection method comprising:
acquiring an infrared image of a target area;
extracting a gas cloud image area of a gas cloud formed with a leaked gas on the basis of the infrared image of the target area acquired in the acquiring of an infrared image of a target area;
acquiring a gas temperature of the gas cloud;
obtaining a concentration-thickness product of the gas cloud; and obtaining a reliability degree that is an index representing the degree of reliability with respect to the concentration-thickness product of the gas cloud obtained in the obtaining of a concentration-thickness product on the basis of a background temperature in the gas cloud image area extracted in the extracting and the gas temperature acquired in the acquiring of a gas cloud temperature.

* * * * *